United States Patent [19]

Jähne

[11] Patent Number: 5,359,067
[45] Date of Patent: Oct. 25, 1994

[54] PROCESS FOR THE PREPARATION OF 5-SUBSTITUTED CYTOSINES AND OTHER 4,5-DISUBSTITUTED PYRIMIDIN-2(1H)-ONES, AND INTERMEDIATES ARISING IN THE COURSE OF THIS

[75] Inventor: Gerhard Jähne, Frankfurt am Main, Fed. Rep. of Germany

[73] Assignee: Hoechst Aktiengesellschaft, Frankfurt am Main, Fed. Rep. of Germany

[21] Appl. No.: 978,730

[22] Filed: Nov. 19, 1992

[30] Foreign Application Priority Data

Nov. 23, 1991 [DE] Fed. Rep. of Germany ....... 4138585

[51] Int. Cl.$^5$ .............................. C07D 239/36
[52] U.S. Cl. .................... 544/317; 544/309; 544/314
[58] Field of Search ............... 544/315, 316, 317, 318, 544/333, 313, 309, 314

[56] References Cited

PUBLICATIONS

Some Pyrimidine Derivatives, J. L. Rabinowitz et al., J. Am. Chem. Soc., 75:5758–5759 (1953).
Synthesis of N-(2,3-Dihydroxypropyl) Derivatives of Nucleic Bases, Ueda et al., J. Heterocyclic Chem., 8:827–829 (1971).

(List continued on next page.)

*Primary Examiner*—John M. Ford
*Attorney, Agent, or Firm*—Finnegan, Henderson, Farabow, Garrett & Dunner

[57] ABSTRACT

Process for the preparation of 5-substituted cytosines and other 4,5-disubstituted pyrimidin-2(1H)-ones, and intermediates arising in the course of this The process for the preparation of compounds of the formula I,

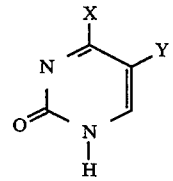

wherein compounds of the formula II

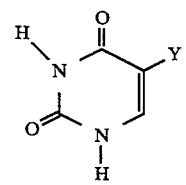

are converted into an azole derivative of the formula III or an azine derivative of the formula IV

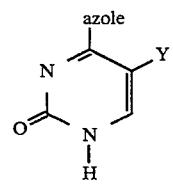

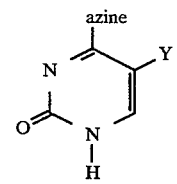

which can subsequently be converted into a compound of the formula I using a nucleophile XH.

8 Claims, No Drawings

PUBLICATIONS

Chemical Conversion of Thymidine Into 5-Methyl-2'-deoxycytidine, W. L. Sung, J.C.S. Chem., Comm. 1089 (1981).

4-(1,2,4-Triazol-1-yl)- and 4-(3-Nitro-1,2,4-triazol-1-yl)-1-(β-D-2,3,5-tri-O-acetylarabinofuranosyl)pyrimidin-2(1H)-ones. Valuable Intermediates in The Synthesis of Derivatives of 1-(β-D-Arabinofuranosyl)cytosine (Ara-C), K. J. Divakar et al., J.C.S. Perkin I, 1171–1176 (1982).

Studies of Antitumor-Active 5-Fluorouracil Derivatives. I. Synthesis of N-Phthalidyl 5-Fluorouracil Derivatives, S. Kamata et al., Chem. Pharm. Bull., 33(8):3160–3175 (1985).

Grabowicz et al., 5-Fluorocytosine from 5-fluorouracil, Chemical Abstracts, vol. 100, 1984, p. 602, abstract No. 209860h.

Jähne et al., Preparation of Carbocyclic Phosphonate Nucleosides, Tetrahedron Letters, vol. 33, No. 37, pp. 5335–5338, 1992.

PROCESS FOR THE PREPARATION OF 5-SUBSTITUTED CYTOSINES AND OTHER 4,5-DISUBSTITUTED PYRIMIDIN-2(1H)-ONES, AND INTERMEDIATES ARISING IN THE COURSE OF THIS

The present invention relates to a process for the preparation of 5-substituted cytosines and other 4,5-disubstituted pyrimidin-2(1H)-ones, and to intermediates arising in the course of this.

The alkylation of heterocyclic nitrogen-containing bases such as uracil, thymine and other 5-substituted uracils generally gives a difficult-to-separate mixture of products monosubstituted on N1 and N3 together with products disubstituted on N1 and N3 (see for example J. L. Rabinowitz and S. Gurin: J. Am. Chem. Soc. 75,5758 (1953); S. Kamata, N. Haga, T. Matsui and W. Nagata: Chem. Pharm. Bull. 33,3160 (1985); N. Ueda, T. Kawabata and K. Takemoto: J. Heterocyclic Chem. 8,827 (1971)). The comparable reaction with cytosine, on the other hand, proceeds with high regioselectivity on N1. It is known that uracil derivatives alkylated on N1, such as for example triacetyluridine or diacetylthymidine can be converted, via the conversion into the 4-(3-nitro-1,2,4-triazol-1-yl) or the 4-(1,2,4-triazol-1-yl) derivatives, into the corresponding 4-amino-, 4-alkylamino-, 4-dialkylamino or 4-arylamino compounds (see for example K. J. Divakar, C. B. Reese: J. Chem. Soc. Perkin Trans. 1, 1982, 1171; W. L. Sung: J. Chem. Soc. Chem. Commun., 1981, 1089). It is further known that cytosine derivatives can be converted to uracil derivatives by means of reaction with sodium nitrite and acid.

Thus, by means of selective alkylation on N1 of cytosine or of 5-substituted cytosines and subsequent reaction with sodium nitrite/acid, uracils alkylated on N1 or 5-substituted uracils alkylated on N1 can be synthesized.

It has now surprisingly been found that uracil not alkylated in the N1 position and 5-substituted uracils not alkylated in the N1 position can also be converted into the corresponding pyrimidines substituted in position 4 by oxygen, sulfur or nitrogen.

The invention accordingly provides a process for the preparation of pyrimidines of the formula I

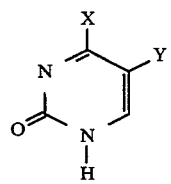

where X is amino, alkylamino, dialkylamino, hydrazino, N2-alkylhydrazino, N2-dialkylhydrazino, alkenylamino, alkynylamino, benzylamino (which may be ring-substituted), dialkenylamino, dialkynylamino, dibenzylamino (which may be ring-substituted), phenylamino (which may be ring-substituted), alkoxy, alkenyloxy, alkynyloxy, benzyloxy (which may be ring-substituted), phenyloxy (which may be ring-substituted), mercapto, alkylthio, alkenylthio, alkynylthio, phenylthio (which may be ring-substituted) or benzylthio (which may be ring-substituted)
and Y is hydrogen, $C_1$–$C_6$-alkyl, $C_1$–$C_5$-cycloalkyl, benzyl (which may be ring-substituted), benzyloxymethyl (which may be ring-substituted), halogen, ethenyl, ethynyl, (E)-2-bromovinyl, vinyl, (E)-2-alkoxycarbonylvinyl or propargyl, which comprises reacting a pyrimidine of the formula II

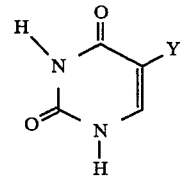

where Y has the abovementioned meanings, with a 5- or 6-membered nitrogen-containing heterocycle and a phosphoric acid halide in an aprotic solvent with addition of a nitrogen-containing base to give an azole intermediate of the formula III

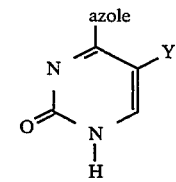

or an azine intermediate of the formula IV

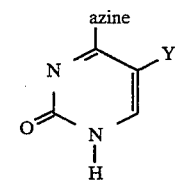

where Y has the abovementioned meanings, which intermediate is reacted as a crude product or isolated intermediate compound with the NH, OH or SH nucleophiles corresponding to the radical X (i.e. with ammonia, alkylamine, dialkylamine, etc.) to give compounds of the formula I, in which X and Y have the abovementioned meanings.

The process according to the invention for the preparation of pyrimidines of the formula I is of particular importance A) where X is amino, alkylamino, dialkylamino, hydrazino, benzylamino, alkoxy, benzyloxy, mercapto, alkylthio or benzylthio and Y is hydrogen, $C_1$–$C_6$-alkyl, benzyl, benzyloxymethyl, fluorine, chlorine, bromine, (E)-2-bromovinyl, ethynyl or propargyl.

The process according to the invention for the preparation of pyrimidines of the formula I is of very particular importance B) where X is amino, alkylamino, dialkylamino or benzylamino, in particular amino and Y is $C_1$–$C_6$-alkyl, fluorine or chlorine, in particular methyl. The resultant intermediates of the formula IIIa

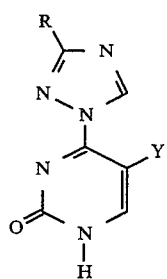

in which R is hydrogen or nitro or the triazole radical is replaced by an N-methylimidazole radical and in which Y has the meanings defined under B), are likewise a subject of the present invention.

The process according to the invention is suitable in particular for the preparation of 5-methyl-cytosine (compound of the formula I, in which X is amino and Y is methyl). The resultant intermediate of the formula IIIb

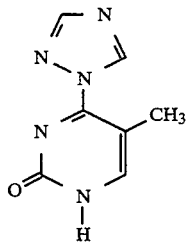

is likewise a subject of the present invention.

The alkyl, alkenyl and alkynyl groups mentioned as substituents or substituents of substituents (for example in the substituents alkylamino, alkoxy, etc.) can be straight-chain, branched or cyclic. They preferably contain up to 8 carbon atoms, preferably up to 6, in particular up to 3, carbon atoms.

Suitable alkyl groups are for example methyl, ethyl, propyl, isopropyl or cyclopentyl; suitable alkenyl groups are for example propenyl, 1-isobuten-3-yl or 1-cyclopenten-3-yl; suitable alkynyl groups are for example 1-propyn-3-yl or 1-butyn-4-yl. The above-listed aromatic radicals of the substituents X and Y can be ring-substituted, for example by $C_1$-$C_5$-alkyl, nitro, halogen or $C_1$-$C_5$-alkoxy, preferably by $C_1$-$C_3$-alkyl, chlorine or $C_1$-$C_3$-alkoxy. The abovementioned 5- or 6-membered nitrogen-containing heterocycle is preferably 1,2,4-triazole, 3-nitro-1,2,4-triazole, N-methylimidazole or pyridine, in particular 1,2,4-triazole.

The phosphoric acid halide used for the reaction is preferably a phosphoric acid chloride; particular preference is given to phosphoryl trichloride and diphenyl chlorophosphate. The aprotic solvent suitable for the reaction is preferably methylene chloride, chloroform, 1,2-dichloroethane, acetonitrile or dioxane.

The nitrogen-containing base which is added to the reaction mixture is preferably a $C_1$-$C_6$-trialkylamine, particularly preferably a $C_1$-$C_3$-trialkylamine, in particular triethylamine.

Suitable stoichiometric ratios of the reactants are for example 0.15-0.5 equivalent of the pyrimidine of the formula II to 0.9-1.3 equivalents of the nitrogen-containing heterocycle, with 0.3-1.1 equivalents of phosphoric acid halide and 0.8-1.5 equivalents of the nitrogen-containing base. Particular preference is given to 0.15-0.5 equivalent of the pyrimidine of the formula II, one equivalent of the nitrogen-containing heterocycle, 0.33-0.99 equivalent of phosphoric acid halide and 1.5 equivalents of the nitrogen-containing base.

The reaction expediently takes place at temperatures of between 0° and 90° C. and is complete after about 2-48 hours.

The process according to the invention is illustrated in more detail by the examples below and also by the patent claims:

EXAMPLE 1

Preparation of the 1,2,4-triazol-1-yl intermediate of the formula III b (phosphoryl trichloride method):

50.6 g (0.33 mol) of phosphoryl trichloride are added under a protecting gas (nitrogen) to a suspension of 69 g (1 mol) of 1,2,4-triazole in 800 ml of dry acetonitrile at an internal temperature of 0°-50° C. During a period of 1 hour, 101.2 g (1 mol) of triethylamine are then added dropwise. After stirring for a further 40 minutes at room temperature, 18.9 g (0.15 mol) of thymine are added. The suspension is stirred for 24 hours at room temperature, 25 ml of water are added and the mixture is stirred for a further 10 minutes and then filtered. The yellow residue is suspended in 400 ml of water, stirred and filtered off by suction after 1 hour. 1.72 g of 5-methyl-4-(1,2,4-triazol-1-yl)-pyrimidin-2-(1H)-one are obtained as a yellow powder with melting point 258°-264° C. The acetonitrile solution is concentrated, the residue is suspended in 400 ml of water, stirred and filtered off by suction. In this manner, a further 7.21 g of the compound are obtained. The title compound can be recrystallized from dimethylformamide and then melts at 275°-280° C. $^1$H NMR (60 MHz, $d_6$-DMSO), δ[ppm]: approx. 12.0 (s, broad, 1H), 9.33 (s, 1H), 8.40 (s, 1H), 8.13 (s, 1H), 2.3 (s, 3H).

Two by-products are isolated from the mother liquors by chromatographic separation on silica gel using dichloromethane/methanol 9/1 as the mobile phase:

By-product I: 2,4-bis(1,2,4-triazol-1-yl)-5-methyl-pyrimidine, colorless powder, melting point: 193°-196° C., $^1$H NMR (270 MHz, $d_6$-DMSO), δ[ppm]: 9.76 (s, 1H), 9.74 (s, 1H), 9.01 (s, 1H), 8.46 (s, 1H), 8.36 (s, 1H), 2.64 (s, 3H).

By-product II: 5-methyl-2-(1,2,4-triazol-4-yl)-4-(1,2,4-triazol-1-yl)-pyrimidine, colorless crystals, melting point: 256°-261° C., $^1$H NMR (270 MHz, $d_6$-DMSO), 67[ppm]: 9.92 (s, 1H), 9.52 (s, 2H), 8.99 (s, 1H), 8.46 (s, 1H), 2.63 (s, 3H).

By means of treatment with 1N sodium hydroxide solution (6 hours, 30°-50° C.), both compounds can be converted into 5-methyl-4-(1,2,4-triazol-1-yl)-pyrimidin-2-(1H)-one.

EXAMPLE 2

Preparation of the 1,2,4-triazol-1-yl intermediate of the formula III b (diphenyl chlorophosphate method):

69 g (1 mol) of 1,2,4-triazole are suspended in 800 ml of dry acetonitrile under a protecting gas (argon). 251 g (0.95 mol) of diphenyl chlorophosphate are added to the suspension at 0°-10° C. Subsequently, in the course of 1 hour, 151.79 g (1.5 mol) of triethylamine are added dropwise before 63 g (0.5 mol) of thymine are added. The resulting suspension is stirred for 12 hours at room temperature. Finally, the mixture is heated for 5 hours at 60°-80° C. 40 ml of methanol are added to the cooled suspension and the mixture is stirred for 2 hours at room temperature. The suspension is filtered; the residue is stirred with one liter of diisopropyl ether, filtered off again by suction and stirred with 800 ml of water. The aqueous suspension is filtered and the solid residue is recrystallized from 1300 ml of dimethylformamide. 28.6 g of 5-methyl-4-(1,2,4-triazol-1-yl)pyrimdin-2(1H)-one are obtained with melting point 275°–280° C.

EXAMPLE 3

Preparation of 5-methyl-cytosine (compound of the formula I, in which X is amino and Y is methyl) from a compound: of the formula III b 1.06 g (6 mmol) of 5-methyl-4-(1,2,4-triazol-1-yl)-pyrimidin-2(1H)-one are dissolved in 30 ml of concentrated aqueous ammonia and stirred for 3 hours at reflux temperature. The cooled solution is evaporated to dryness, the residue is dissolved in hot water, the solution is cooled and three times the amount of acetone are added. The precipitate is filtered off by suction and is dried in vacuo. 0.73 g (97.3% of theory) of 5-methyl-cytosine is obtained as a colorless powder with melting point 271°–274° C.

EXAMPLE 4

Preparation of N4-methyl-5-methylcytosine (compound of the formula I, in which X is methylamino and Y is methyl): from a compound of the formula III b 1.06 g (6mmol) of 5-methyl-4-(1,2,4-triazol-1-yl)-pyrimidin-2(1H)-one are dissolved in 20 ml of 40% strength aqueous methylamine solution and the solution is stirred for 5 hours at room temperature. The solution is concentrated and chromatographed on silica gel using ethyl acetate/methanol 2/1. 0.67 g (80.3% of theory) of N4-methyl-5-methylcytosine is obtained as a colorless powder with melting point of 160°–165° C. (decomp.). $^1$H NMR, d$_6$-DMSO, δ[ppm]: 10.4 (s, 1H) 7.17 (s, 1H), 7.1 (s, broad, 1H), 2.8 (d, 3H), 1.82 (d, 3H).

EXAMPLE 5

Preparation of 4-methoxy-5-methylpyrimidin-2(1H)-one (compound of the formula I, in which X is methoxy and Y is methyl) from a compound of the formula III b:

1.06 g (6 mmol) of 5-methyl-4-(1,2,4-triazol-1-yl)-pyrimidin-2(1H)-one are boiled under reflux with 972 mg (18 mmol) of sodium methylate in 30 ml of anhydrous methanol for 4 hours with exclusion of moisture. The cooled solution is neutralized with acetic acid, concentrated and chromatographed on silica gel using ethyl acetate/methanol 9/1. 770 mg (91.7% of theory) of 4-methoxy-5-methylpyrimidin-2(1H)-one are obtained with melting point 196°–199° C. $^1$H NMR (270 MHz, d$_6$-DMSO), δ[ppm]: 11.09 (s, 1H), 7.51 (d, 1H), 3.83 (s, 3H), 1.85 (s, 3H).

EXAMPLE 6

Preparation of 4-isopropoxy-5-methyl-pyrimidin-2(1H)-one (compound of the formula I, in which X is isopropoxy and Y is methyl) from a compound of the formula III b:

1.06 g (6 mmol) of 5-methyl-4-(1,2,4-triazol-1-yl)-pyrimidin-2(1H)-one are added to a solution of 1,476 g (18 mmol) of sodium isopropylate in 30 ml of anhydrous isopropanol and the mixture is stirred for 4 hours at 50° C. The solution obtained is neutralized with cooling using acetic acid, concentrated and chromatographed on silica gel using dichloromethane/methanol 9/1. The eluate is concentrated, stirred with ether and 0.71 g (70.4% of theory) of 4-isopropoxy-5-methyl-pyrimidin-2(1H)-one with melting point 206°–207° C. is obtained as residue. $^1$H NMR (270 MHz, d$_6$-DMSO), δ[ppm]: 11.02 (s, 1H), 7.48 (s, 1H), 5.25 (m, 1H), 1.81 (s, 3H), 1.27 (d, 6H).

EXAMPLE 7

Preparation of 4-benzyloxy-5-methylpyrimidin-2(1H)-one (compound of the formula I, in which X is benzyloxy and Y is methyl) from a compound of the formula III b:

1.06 g (6 mmol) of 5-methyl-4-(1,2,4-triazol-1-yl)-pyrimidin-2(1H)-one are added to a solution of 2.34 g (18 mmol) of sodium benzylate in 25 ml of dry benzyl alcohol and 25 ml of dry dimethylformamide are added. The mixture is heated for 2 hours with stirring to 100° C. The cooled solution is neutralized with acetic acid, concentrated and chromatographed on silica gel using ethylacetate/methanol 9/1. 880 mg (67.9% of theory) of 4-benzyloxy-5-methylpyrimidin-2(1H)-one are obtained with melting point 181°–182°C. $^1$H NMR (270 MHz, d$_6$-DMSO), δ[ppm]: 11.14 (s, 1H), 7.56 (d, 1H), 7.41 (m, 5H), 5.35 (s, 2H), 1.87 (s, 3H).

EXAMPLE 8

Preparation of 4-ethylthio-5-methylpyrimidin-2(1H)-one (compound of the formula I, in which X is ethylthio and Y is methyl) from a compound of the formula III b:

786 mg (18 mmol) of a 55% strength sodium hydride emulsion are added to 0.7 ml (9 mmol) of ethylmercaptan in 25 ml of dry dimethylformamide at 0° C. and the mixture is stirred for 30 minutes at 0° C. 1.06 g (6 mmol) of 5-methyl-4-(1,2,4-triazol-1-yl)-pyrimidin-2(1H)-one are then added and the mixture is stirred for 3 hours at room temperature. The reaction mixture is neutralized by addition of acetic acid, concentrated and chromatographed on silica gel using dichloromethane/methanol 20/1. 0.64 g (62.7% of theory) of 4-ethylthio-5-methyl-pyrimidin-2(1H)-one is obtained with melting point 181°–184° C. $^1$H NMR (60 MHz, d$_6$-DMSO), δ[ppm]: 11.45 (s, 1H), 7.55 (s, 1H), 3.10 (q, 2H), 1.90 (s, 3H), 1.25 (t, 3H).

I claim:

1. A process for the preparation of a pyrimidine of the formula I,

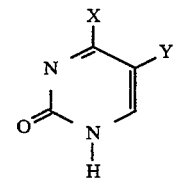

where X is amino, alkylamino, dialkylamino, hydrazino, N2-alkylhydrazino, N2-dialkylhydrazino, alkenylamino, alkynylamino, benzylamino, dialkenylamino, dialkynylamino, dibenzylamino, phenylamino, alkoxy, alkenyloxy, alkynyloxy, benzyloxy, phenyloxy, mercapto, alkylthio, alkenylthio, alkynylthio, phenylthio or benzylthio, wherein the alkyl, alkenyl and alkynyl groups in the foregoing substituents contain up to 8 carbon atoms, and Y is hydrogen, $C_1$–$C_6$-alkyl, $C_1$–$C_5$-cycloalkyl, benzyl, benzyloxymethyl, halogen, ethenyl, ethynyl, (E)-2-bromovinyl, vinyl, (E)-2-alkoxycarbonylvinyl or propargyl, wherein the benzylamino, dibenzylamino, phenylamino, benzyloxy, phenyloxy, phenylthio, benzylthio, benzyl and benzyloxymethyl substituents X and Y may be ring-substituted by $C_1$–$C_5$-alkyl, nitro. halogen or $C_1$–$C_5$-alkoxy, which comprises reacting a pyrimidine of the formula II

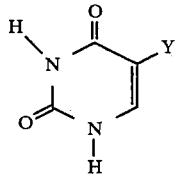

where Y has the abovementioned meanings, with a nitrogen-containing heterocycle selected from the group consisting of 1,2,4-triazole, 3-nitro-1,2,4-triazole, N-methylimidazole and pyridine and a phosphoric acid halide in an aprotic solvent with addition of a nitrogen-containing base to give an azole intermediate of the formula III

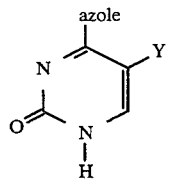

or an azine intermediate of the formula IV

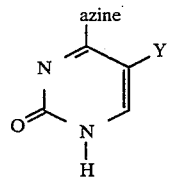

where Y has the abovementioned meanings, and reacting said azole intermediate or said azine intermediate with the amino, alkylamino, dialkylamino, hydrazino, benzylamino, dialkenylamino, dialkynylamino, dibenzylamino, phenylamino, alkoxy, alkenyloxy, alkynyloxy, benzyloxy, phenyloxy, mercapto, alkylthio, alkenylthio, alkynylthio, phenylthio or benzylthio nucleophiles corresponding to the radical X to give compounds of the formula I, in which X and Y have the abovementioned meanings.

2. The process as claimed in claim 1, wherein, in the compounds of the formula I,
X is amino, alkylamino, dialkylamino, hydrazino, benzylamino, alkoxy, benzyloxy, mercapto, alkylthio or benzylthio and
Y is hydrogen, $C_1$–$C_6$-alkyl, benzyl, benzyloxymethyl, fluorine, chlorine, bromine, (E)-2-bromovinyl, ethynyl or propargyl.

3. The process as claimed in claim 1, wherein, in the compounds of the formula I,
X is amino, alkylamino, dialkylamino or benzylamino and Y is $C_1$–$C_6$-alkyl, fluorine or chlorine.

4. The process as claimed in claim 1, wherein, in the compound of the formula I,
X is amino and Y is methyl.

5. The process as claimed in claim 1, wherein the phosphoric acid halide is phosphoryl trichloride or diphenyl chlorophosphate.

6. The process as claimed in claim 1, wherein 0.15–0.5 equivalent of the pyrimidine of the formula II is reacted with 0.9–1.3 equivalents of the nitrogen-containing heterocycle, with 0.3–1.1-equivalents of phosphoric acid halide and 0.8–1.5 equivalents of the nitrogen-containing base.

7. A compound of the formula IIIa

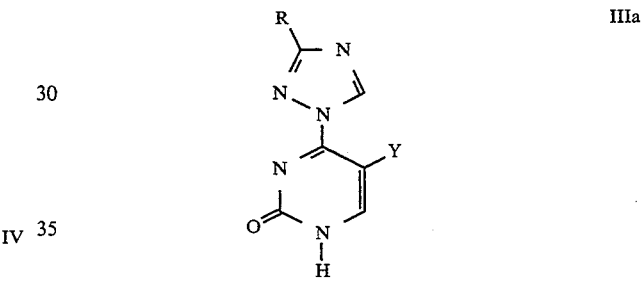

where R is hydrogen or nitro and Y is $C_1$–$C_6$ alkyl, fluorine or chlorine.

8. A compound of the formula IIIb

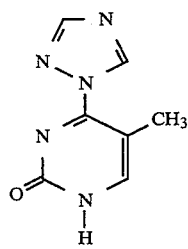

* * * * *